(12) United States Patent
Chen et al.

(10) Patent No.: US 12,404,612 B2
(45) Date of Patent: Sep. 2, 2025

(54) FABRIC WITH ELECTRICAL COMPONENTS

(71) Applicant: Apple Inc., Cupertino, CA (US)

(72) Inventors: Yue Chen, Saratoga, CA (US); Didio V Gomes, Sunnyvale, CA (US); Benjamin J Grena, San Francisco, CA (US); Storrs T Hoen, Brisbane, CA (US); David M Kindlon, Felton, CA (US); Daniel A Podhajny, Morgan Hill, CA (US); Andrew L Rosenberg, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 87 days.

(21) Appl. No.: 17/862,249

(22) Filed: Jul. 11, 2022

(65) Prior Publication Data

US 2023/0061553 A1    Mar. 2, 2023

Related U.S. Application Data

(60) Provisional application No. 63/238,615, filed on Aug. 30, 2021.

(51) Int. Cl.
*D03D 1/00*    (2006.01)
*A41D 1/00*    (2018.01)
(Continued)

(52) U.S. Cl.
CPC ........... *D03D 1/0088* (2013.01); *A41D 1/005* (2013.01); *A41D 27/205* (2013.01); *A61B 5/27* (2021.01);
(Continued)

(58) Field of Classification Search
CPC .... D03D 1/0088; A41D 1/002; A41D 27/205; D10B 2401/18; D10B 2403/02431; A61B 5/27; A61B 5/6804
See application file for complete search history.

(56) References Cited

U.S. PATENT DOCUMENTS 6,563,424 B1 *   5/2003   Kaario .................... G06F 1/163
                                                            340/572.1
7,462,035 B2 * 12/2008   Lee ....................... H01R 12/592
                                                                439/37
(Continued)

*Primary Examiner* — Jennifer A Steele
(74) *Attorney, Agent, or Firm* — Treyz Law Group, P.C.; Kendall P. Woodruff

(57) ABSTRACT

One or more electrical components may be incorporated into a piece of fabric. The electrical component may include an internal portion that is located inside of the fabric, an external portion that is located on an exterior surface of the fabric, and protrusions that extend through the fabric to electrically and/or mechanically couple the internal and external portions of the electrical component. The internal portion of the component may be inserted into the fabric during formation of the fabric. The external portion of the component may be coupled to the internal portion after the fabric is formed by inserting the protrusions on the internal portion into recesses in the external portion. The external portion of the component may contain skin-facing and/or viewer-facing input-output devices, while the internal portion may contain circuitry that electrically communicates with the input-output devices in the external portion.

19 Claims, 12 Drawing Sheets

(51) Int. Cl.
  *A41D 27/20* (2006.01)
  *A61B 5/00* (2006.01)
  *A61B 5/27* (2021.01)

(52) U.S. Cl.
  CPC ........ *A61B 5/6831* (2013.01); *D10B 2401/16* (2013.01); *D10B 2401/18* (2013.01); *D10B 2509/00* (2013.01)

(56) References Cited

U.S. PATENT DOCUMENTS

| | | | |
|---|---|---|---|
| 9,282,893 | B2 | 3/2016 | Longinotti-Buitoni et al. |
| 9,592,007 | B2 | 3/2017 | Nuovo et al. |
| 10,197,417 | B2 | 2/2019 | Logan et al. |
| 10,503,339 | B2 | 12/2019 | Karagozler |
| 10,772,209 | B2 | 9/2020 | Sunshine et al. |
| 10,795,438 | B2 | 10/2020 | Wang |
| 2003/0108217 | A1* | 6/2003 | Tilbury .................. H04R 1/028 381/388 |
| 2003/0211797 | A1 | 11/2003 | Hill et al. |
| 2004/0125515 | A1* | 7/2004 | Popovich ............. D03D 1/0088 361/1 |
| 2013/0338472 | A1* | 12/2013 | Macia ................ A61B 5/02055 174/255 |
| 2014/0070957 | A1* | 3/2014 | Longinotti-Buitoni ...................... A61B 5/02055 340/870.01 |
| 2015/0370320 | A1 | 12/2015 | Connor |
| 2016/0320037 | A1* | 11/2016 | Wong .................... H05K 1/038 |
| 2017/0244208 | A1* | 8/2017 | Barth .................. A44B 17/0064 |
| 2018/0084643 | A1* | 3/2018 | Baxi ...................... H05K 1/112 |
| 2019/0021407 | A1* | 1/2019 | Howland ................ A41D 1/005 |
| 2019/0132948 | A1* | 5/2019 | Longinotti-Buitoni ...................... A61B 5/6805 |
| 2019/0297961 | A1* | 10/2019 | Strecker ................ A61B 5/6804 |

* cited by examiner

FABRIC WITH ELECTRICAL COMPONENTS

This application claims the benefit of provisional patent application No. 63/238,615, filed Aug. 30, 2021, which is hereby incorporated by reference herein in its entirety.

FIELD

This relates generally to items with fabric and, more particularly, to items with fabric and electrical components.

BACKGROUND

It may be desirable to form bags, furniture, clothing, and other items from materials such as fabric. Fabric items generally do not include electrical components. It may be desirable, however, to incorporate electrical components into fabric to provide a user of a fabric item with enhanced functionality.

It can be challenging to incorporate electrical components into fabric. Fabric is flexible, so it can be difficult to mount structures to fabric. Electrical components must be coupled to signal paths (e.g., signal paths that carry data signals, power, etc.), but unless care is taken, signal paths may be damaged, or components may become dislodged as fabric is bent or stretched.

It would therefore be desirable to be able to provide improved techniques for incorporating electrical components into items with fabric.

SUMMARY

Interlacing equipment (e.g., weaving equipment, knitting equipment, braiding equipment, etc.) may be provided with individually adjustable components. The use of individually adjustable components may allow electrical components to be inserted into and/or embedded in the fabric during the creation or formation of the fabric.

The interlacing equipment may create a gap between first and second fabric portions during interlacing operations. The gap may be a void between fabric portions or the gap may be a position or location between fabric portions. An insertion tool may insert an electrical component into the gap, and the electrical component may be electrically coupled to conductive strands in the gap, if desired.

An electrical component may include an internal portion that is located inside of the fabric, an external portion that is located on an exterior surface of the fabric, and protrusions that extend through the fabric to electrically and/or mechanically couple the internal and external portions of the electrical component. The internal portion of the component may be inserted into the fabric during formation of the fabric. After the fabric is formed, protrusions on the internal portion may extend through the fabric and may be exposed to the exterior of the fabric. The external portion of the component may then be coupled to the internal portion by attaching the protrusions to mating attachment structures (e.g., recesses) on the external portion of the fabric.

The external portion of the component may contain skin-facing and/or viewer-facing input-output devices (e.g., a heart-rate sensor, a blood oxygen sensor, a microphone, a speaker, a display, an indicator, a touch screen, a button, etc.), while the internal portion may contain circuitry that electrically communicates with the input-output device(s) in the external portion.

The fabric may be used to form a wrist strap or other wearable item.

DETAILED DESCRIPTION

Electronic devices, enclosures, and other items may be formed from fabric such as woven fabric, knit fabric, or other suitable fabric. The fabric may include strands of insulating and conductive material. Conductive strands may form signal paths through the fabric and may be coupled to electrical components such as light-emitting diodes and other light-emitting devices, integrated circuits, sensors, haptic output devices, and other circuitry.

Interlacing equipment (sometimes referred to as intertwining equipment) may include weaving equipment, knitting equipment, braiding equipment, or any other suitable equipment used for crossing, looping, overlapping, or otherwise coupling strands of material together to form a network of strands (e.g., fabric). Interlacing equipment may be provided with individually adjustable components such as warp strand positioning equipment (e.g., heddles or other warp strand positioning equipment), weft strand positioning equipment, a reed, take-down equipment, let off equipment (e.g., devices for individually dispensing and tensioning warp strands), needle beds, feeders, guide bars, strand processing and component insertion equipment, and other components for forming fabric items. The individual adjustability of these components may allow interlacing operations (e.g., weaving operations, knitting operations, braiding operations, and/or other interlacing operations) to be performed without requiring continuous lock-step synchronization of each of these devices, thereby allowing fabric with desired properties to be woven. As an example, normal reed movement and other weaving operations may be periodically suspended and/or may periodically be out-of-sync with other components to accommodate component insertion operations whereby electrical components (sometimes referred to as nodes or smart nodes) are inserted into the fabric during the creation or formation of the fabric.

Figure 1:
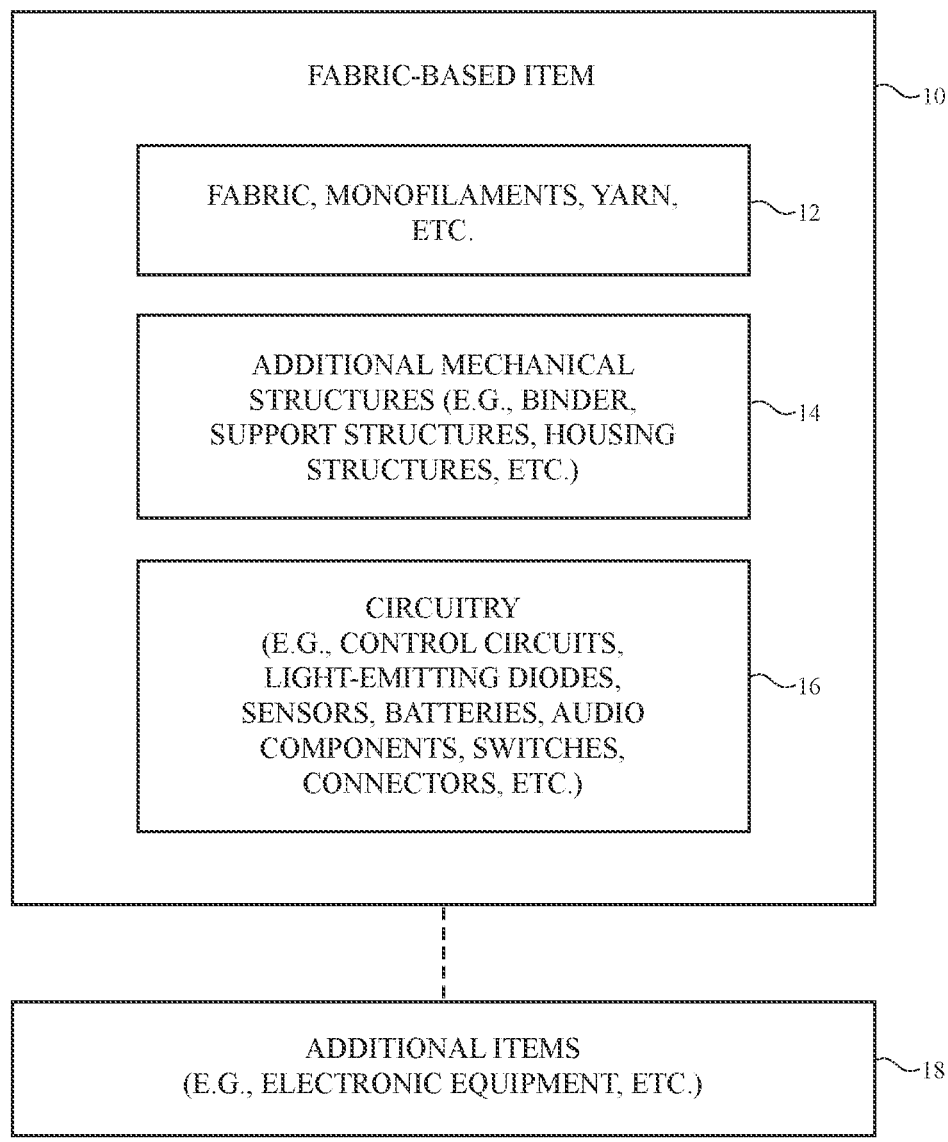
FIG. 1 is a schematic diagram of an illustrative fabric item in accordance with an embodiment.

Items such as item 10 of FIG. 1 may include fabric and may sometimes be referred to as a fabric item or fabric-based item. Item 10 may be an electronic device or an accessory for an electronic device such as a laptop computer, a computer monitor containing an embedded computer, a tablet computer, a cellular telephone, a media player, or other handheld or portable electronic device, a smaller device such as a wrist-watch device, a pendant device, a headphone or earpiece device, a device embedded in eyeglasses or other equipment worn on a user's head, or other wearable or miniature device, a television, a computer display that does not contain an embedded computer, a gaming device, a navigation device, an embedded system such as a system in which fabric item 10 is mounted in a kiosk, in an automobile, airplane, or other vehicle (e.g., an autonomous or non-autonomous vehicle), other electronic equipment, or equipment that implements the functionality of two or more of these devices. If desired, item 10 may be a removable external case for electronic equipment, may be a strap, may be a wrist band or head band, may be a removable cover for a device, may be a case or bag that has straps or that has other structures to receive and carry electronic equipment and other items, may be a necklace or arm band, may be a wallet, sleeve, pocket, or other structure into which electronic equipment or other items may be inserted, may be part of a chair, sofa, or other seating (e.g., cushions or other seating structures), may be part of an item of clothing or other wearable item (e.g., a hat, belt, wrist band, headband, etc.), or may be any other suitable item that incorporates fabric.

Item 10 may include interlaced strands of material such as monofilaments and yarns that form fabric 12. As used herein, "interlaced" strands of material and "intertwined" strands of material may both refer to strands of material that are crossed with one another, looped with one another, overlapping one another, or otherwise coupled together (e.g., as part of a network of strands that make up a fabric). Fabric 12 may form all or part of a housing wall or other layer in an electronic device, may form internal structures in an electronic device, or may form other fabric-based structures. Item 10 may be soft (e.g., item 10 may have a fabric surface that yields to a light touch), may have a rigid feel (e.g., the surface of item 10 may be formed from a stiff fabric), may be coarse, may be smooth, may have ribs or other patterned textures, and/or may be formed as part of a device that has portions formed from non-fabric structures of plastic, metal, glass, crystalline materials, ceramics, or other materials.

The strands of material used in forming fabric 12 may be single-filament strands (sometimes referred to as fibers) or may be threads, yarns, or other strands that have been formed by interlacing multiple filaments of material together. Strands may be formed from polymer, metal, glass, graphite, ceramic, natural materials such as cotton or bamboo, or other organic and/or inorganic materials and combinations of these materials. Conductive coatings such as metal coatings may be formed on non-conductive strands (e.g., plastic cores) to make them conductive. Reflective coatings such as metal coatings may be applied to strands to make them reflective. Strands may also be formed from single-filament metal wire (e.g., bare metal wire), multifilament wire, or combinations of different materials. Strands may be insulating or conductive.

Strands in fabric 12 may be conductive along their entire lengths or may have conductive portions. Strands may have metal portions that are selectively exposed by locally removing insulation (e.g., to form connections with other conductive strand portions and/or to form connections with electrical components). Strands may also be formed by selectively adding a conductive layer to a portion of a non-conductive strand). Threads and other multifilament yarns that have been formed from interlaced filaments may contain mixtures of conductive strands and insulating strands (e.g., metal strands or metal coated strands with or without exterior insulating layers may be used in combination with solid plastic strands or natural strands that are insulating). In some arrangements, which may sometimes be described herein as an example, fabric 12 may be a woven fabric and the strands that make up fabric 12 may include warp strands and weft strands.

Conductive strands and insulating strands may be woven, knit, or otherwise interlaced to form conductive paths. The conductive paths may be used in forming signal paths (e.g., signal buses, power lines for carrying power, etc.), may be used in forming part of a capacitive touch sensor electrode, a resistive touch sensor electrode, or other input-output device, or may be used in forming other patterned conductive structures. Conductive structures in fabric 12 may be used in carrying electrical current such as power, digital signals, analog signals, sensor signals, control signals, data, input signals, output signals, or other suitable electrical signals.

Item 10 may include additional mechanical structures 14 such as polymer binder to hold strands in fabric 12 together, support structures such as frame members, housing structures (e.g., an electronic device housing), and other mechanical structures.

To enhance mechanical robustness and electrical conductivity at strand-to-strand connections and/or strand-to-component connections, additional structures and materials (e.g., solder, crimped metal connections, welds, conductive adhesive such as anisotropic conductive film and other conductive adhesive, non-conductive adhesive, fasteners, etc.) may be used in fabric 12. Strand-to-strand connections may be formed where strands cross each other perpendicularly or at other strand intersections where connections are desired. Insulating material can be interposed between intersecting conductive yarns at locations in which it is not desired to form a strand-to-strand connection. The insulating material may be plastic or other dielectric, may include an insulating strand or a conductive strand with an insulating coating or insulated conductive monofilaments, etc. Solder connections may be formed between conductive strands and/or between conductive strands and electrical components by melting solder so that the solder flows over conductive strands. The solder may be melted using an inductive soldering head to heat the solder, using hot air to heat the solder, using a reflow oven to heat the solder, using a laser or hot bar to heat the solder, or using other soldering equipment. In some arrangements, outer dielectric coating layers (e.g., outer polymer layers) may be melted away in the presence of molten solder, thereby allowing underlying metal yarns to be soldered together. In other arrangements, outer dielectric coating layers may be removed prior to soldering (e.g., using laser ablation equipment or other coating removal equipment).

Circuitry 16 may be included in item 10. Circuitry 16 may include electrical components that are coupled to fabric 12, electrical components that are housed within an enclosure formed by fabric 12, electrical components that are attached to fabric 12 using welds, solder joints, adhesive bonds (e.g., conductive adhesive bonds such as anisotropic conductive adhesive bonds or other conductive adhesive bonds), crimped connections, or other electrical and/or mechanical bonds. Circuitry 16 may include metal structures for carrying current, electrical components such as integrated circuits, light-emitting diodes, sensors, and other electrical devices. Control circuitry in circuitry 16 may be used to control the operation of item 10 and/or to support communications with item 18 and/or other devices.

Item 10 may interact with electronic equipment or other additional items 18. Items 18 may be attached to item 10 or item 10 and item 18 may be separate items that are configured to operate with each other (e.g., when one item is a case and the other is a device that fits within the case, etc.). Circuitry 16 may include antennas and other structures for supporting wireless communications with item 18. Item 18 may also interact with item 10 using a wired communications link or other connection that allows information to be exchanged.

In some situations, item 18 may be an electronic device such as a cellular telephone, computer, or other portable electronic device and item 10 may form a cover, case, bag, or other structure that receives the electronic device in a pocket, an interior cavity, or other portion of item 10. In other situations, item 18 may be a wrist-watch device or other electronic device and item 10 may be a strap or other fabric item that is attached to item 18 (e.g., item 10 and item 18 may together form a fabric-based item such as a wrist-watch with a strap). In still other situations, item 10 may be an electronic device, fabric 12 may be used in forming the electronic device, and additional items 18 may include accessories or other devices that interact with item 10. Signal paths formed from conductive yarns and monofilaments may be used to route signals in item 10 and/or item(s) 18.

The fabric that makes up item 10 may be formed from yarns and/or monofilaments that are interlaced using any suitable interlacing equipment. With one suitable arrangement, which may sometimes be described herein as an example, fabric 12 may be woven fabric formed using a weaving machine. In this type of illustrative configuration, fabric may have a plain weave, a basket weave, a satin weave, a twill weave, or variations of these weaves, may be a three-dimensional woven fabric, or may be other suitable fabric. This is, however, merely illustrative. If desired, fabric 12 may include knit fabric, warp knit fabric, weft knit fabric, braided fabric, other suitable type of fabric, and/or a combination of any two or more of these types of fabric.

Figure 2:
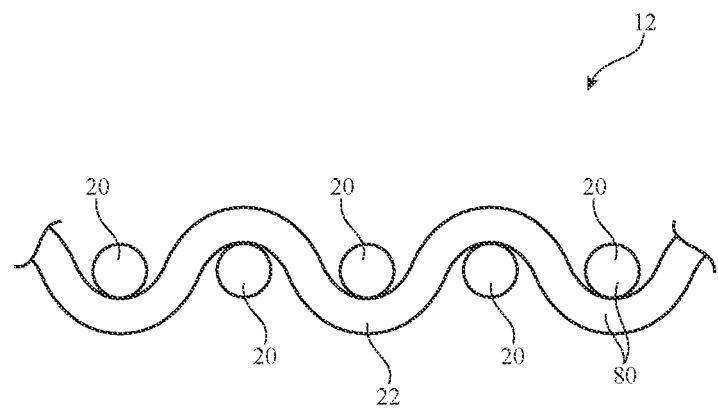
FIG. 2 is a side view of illustrative fabric in accordance with an embodiment.

A cross-sectional side view of illustrative woven fabric 12 is shown in FIG. 2. As shown in FIG. 2, fabric 12 may include strands 80. Strands 80 may include warp strands 20 and weft strands 22. If desired, additional strands that are neither warp nor weft strands may be incorporated into fabric 12. The example of FIG. 2 is merely illustrative. In the illustrative configuration of FIG. 2, fabric 12 has a single layer of woven strands 80. Multi-layer fabric constructions may be used for fabric 12 if desired.

Figure 3:
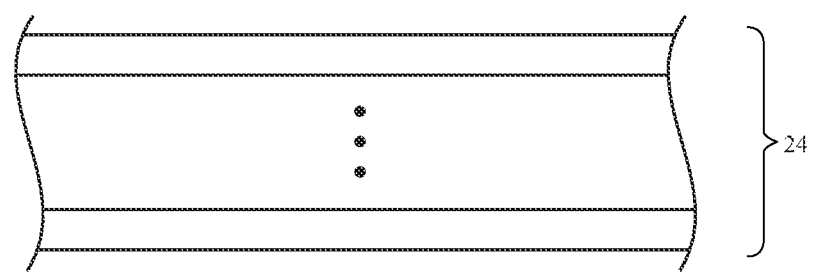
FIG. 3 is a side view of layers of material that may be incorporated into a fabric item in accordance with an embodiment.

Item 10 may include non-fabric materials (e.g., structures formed from plastic, metal, glass, ceramic, crystalline materials such as sapphire, etc.). These materials may be formed using molding operations, extrusion, machining, laser processing, and other fabrication techniques. In some configurations, some or all of item 10 may include one or more layers of material such as layers 24 of FIG. 3. Layers 24 may include layers of polymer, metal, glass, fabric, adhesive, crystalline materials, ceramic, substrates on which components have been mounted, patterned layers of material, layers of material containing patterned metal traces, thin-film devices such as transistors, and/or other layers.

Figure 4:
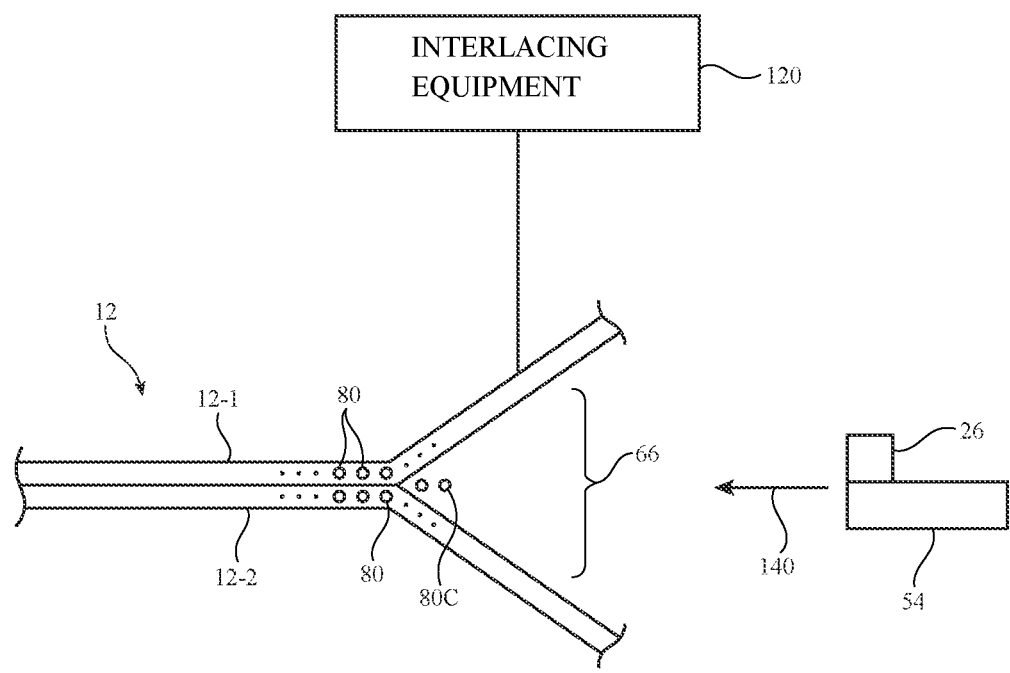
FIG. 4 is a diagram illustrating how interlacing equipment may be used to create fabric while an insertion tool is used to insert one or more electrical components into the fabric in accordance with an embodiment.

A diagram illustrating how electrical components may be inserted into fabric 12 during the formation of fabric 12 is illustrated in FIG. 4. As shown in FIG. 4, fabric 12 may be formed from fabric portions such as fabric portions 12-1 and 12-2. Fabric portions 12-1 and 12-2 may be formed from interlaced strands 80. For example, a first set of strands 80 may be used to form fabric portion 12-1 and a second set of strands 80 may be used to form fabric portion 12-2. Fabric portions 12-1 and 12-2 may be different portions of a single layer of fabric 12, or fabric portion 12-1 may form one or more first layers of fabric 12 and fabric portion 12-2 may form one or more second layers of fabric 12.

Using interlacing equipment 120, strands 80 may be interlaced to form fabric 12. Interlacing equipment 120 may be weaving equipment, knitting equipment, braiding equipment, or other suitable interlacing equipment. Interlacing equipment 120 may be used to create one or more regions in fabric 12 such as pocket 66 (sometimes referred to as a gap, space, cavity, void, position, location, etc.) for receiving electrical components. Regions in fabric 12 that receive electrical components such as pocket 66 may be formed by creating a space or gap between portions of fabric 12 such as fabric portion 12-1 and fabric portion 12-2. The term "pocket" may be used to refer to a void between fabric portions and/or may be used to refer to a position or location between fabric portions (e.g., a position between strands of material in fabric 12, with or without an actual void).

Electrical components may be inserted into pocket 66 during the formation of fabric 12 using component insertion equipment such as insertion tool 54. Insertion tool 54 may hold component 26 and may position component 26 in pocket 66 during interlacing operations (e.g., by moving component 26 towards pocket 66 in direction 140). If desired, component 26 may be electrically and/or mechanically connected to one or more conductive strands 80C in pocket 66. Following insertion and attachment of component 26, interlacing equipment 120 may continue interlacing operations (which may include closing pocket 66, if desired) to continue forming fabric 12.

In some arrangements, processing steps such as alignment of component 26 with conductive strands 80C, electrically connecting (e.g., soldering) component 26 to conductive strands 80C, encapsulation of the electrical connection between component 26 and conductive strands 80C, and/or verification of the integrity of the electrical connection between component 26 and conductive strands 80C may be performed after component 26 is inserted into pocket 66.

In some arrangements, the gap between first and second fabric portions 12-1 and 12-2 may remain in place after electrical component 26 is enclosed in fabric 12 (e.g., a space may exist between fabric portions 12-1 and 12-2 after formation of fabric 12 is complete). In other arrangements, first and second fabric portions 12-1 and 12-2 may be pulled together such that gap 66 is eliminated after electrical component 26 is enclosed in the gap (e.g., fabric portions 12-1 and 12-2 may be in contact with one another without an intervening gap after the formation of fabric 12 is complete). Fabric 12 may have a bulge where electrical component 26 is located, or fabric 12 may not have a bulge where electrical component 26 is located (e.g., the fabric may have substantially uniform thickness across locations with electrical components 26 and locations without electrical components 26, if desired).

Figure 5:
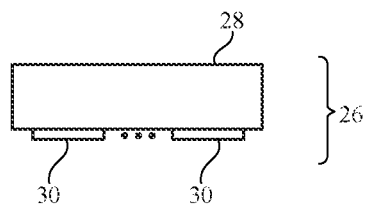
FIG. 5 is a cross-sectional side view of an illustrative electrical component in accordance with an embodiment.

A side view of an illustrative electrical component of the type that may be used in item 10 is shown in FIG. 5. Electrical components in item 10 such as illustrative electrical component 26 of FIG. 5 may include discrete electrical components such as resistors, capacitors, and inductors, may include connectors, may include batteries, may include input-output devices such as switches, buttons, light-emitting components such as light-emitting diodes, audio components such as microphones and speakers, vibrators (e.g., piezoelectric actuators that can vibrate), solenoids, electromechanical actuators, motors, and other electromechanical devices, microelectromechanical systems (MEMs) devices, pressure sensors, light detectors, proximity sensors (light-based proximity sensors, capacitive proximity sensors, etc.), force sensors (e.g., piezoelectric force sensors), strain gauges, moisture sensors, temperature sensors, accelerometers, gyroscopes, compasses, magnetic sensors (e.g., Hall effect sensors and magnetoresistance sensors such as giant magnetoresistance sensors), touch sensors, and other sensors, components that form displays, touch sensor arrays (e.g., arrays of capacitive touch sensor electrodes to form a touch sensor that detects touch events in two dimensions), and other input-output devices, energy storage devices, electrical components that form control circuitry such as non-volatile and volatile memory, microprocessors, application-specific integrated circuits, system-on-chip devices, baseband processors, wired and wireless communications circuitry, and other integrated circuits.

Electrical components such as component 26 may be bare semiconductor dies (e.g., laser dies, light-emitting diode dies, integrated circuits, etc.) or packaged components (e.g. semiconductor dies or other devices packaged within plastic packages, ceramic packages, or other packaging structures).

One or more electrical terminals such as contact pads 30 may be formed on body 28 of component 26. Body 28 (sometimes referred to as device 28, electrical device 28, etc.) may be a semiconductor die (e.g., a laser die, light-emitting diode die, integrated circuit, etc.) or may be a package for a component (e.g., a plastic package or other dielectric package that contains one or more semiconductor dies or other electrical devices). Contacts for body 28 such as pads 30 may be protruding leads, may be planar contacts, may be formed in an array, may be formed on any suitable surfaces of body 28, or may be any other suitable contacts for forming electrical connections to component 26. For example, pads 30 may be metal solder pads.

Figure 6:
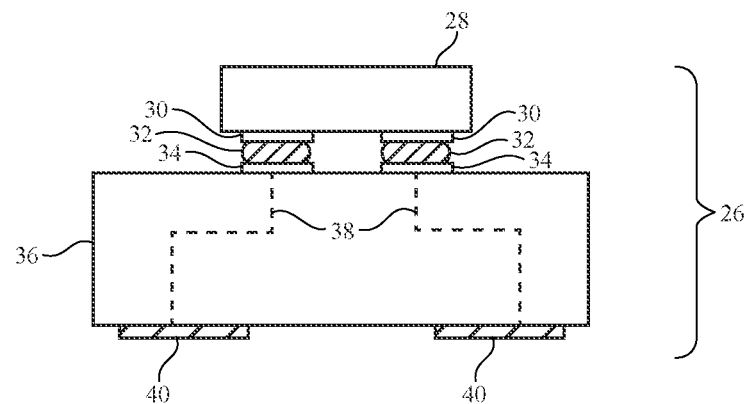
FIG. 6 is a cross-sectional side view of an illustrative electrical component having an electrical device mounted on an interconnect substrate in accordance with an embodiment.

As shown in the example of FIG. 6, body 28 may be mounted on a support structure such as substrate 36. Interposer 36 (sometimes referred to as an interconnect substrate, a printed circuit substrate, etc.) may be a printed circuit, ceramic carrier, or other substrate. The layer(s) forming interconnect substrate 36 may include one or more flexible printed circuit layers such as polyimide layers, one or more layers of rigid printed circuit board material such as fiberglass-filled epoxy (e.g., FR4), and/or layers of other materials (e.g., other dielectric materials such as silicone, other elastomeric material, other flexible polymers, etc.). Interconnect substrate 36 may be larger than body 28 or may have other suitable sizes. Interconnect substrate 36 may have a planar shape with a thickness of 700 microns, more than 500 microns, less than 500 microns, or other suitable thickness. The thickness of body 28 may be 500 microns, more than 300 microns, less than 1000 microns, or other suitable thickness. The footprint (area viewed from above) of body 28 and substrate 36 may be 10 microns×10 microns, 100 microns×100 microns, more than 1 mm×1 mm, less than 10 mm×10 mm, may be rectangular, may be square, may have L-shapes, or may have other suitable shapes and sizes.

Interconnect substrate 36 may contain signal paths such as metal traces 38. Metal traces 38 (sometimes referred to as interconnects, signal paths, etc.) may have portions forming contacts such as pads 34 and 40. Pads 34 and 40 may be formed on the upper surface of interconnect substrate 36, on the lower surface of interconnect substrate 36, and/or on the sides of interconnect substrate 36. Conductive material such as conductive material 32 may be used in mounting body 28 to interconnect substrate 36. Conductive material 32 may be solder (e.g., low temperature solder, high temperature solder, etc.), may be conductive adhesive (isotropic conductive adhesive or anisotropic conductive film), may be formed during welding, and/or may be other conductive material for coupling electrical device pads (body pads) such as pads 30 on body 28 to interconnect substrate pads 34. Metal traces 38 in substrate 36 may couple pads 34 to other pads such as pads 40. If desired, pads 40 may be larger and/or more widely spaced than pads 34, thereby facilitating attachment of substrate 36 to conductive yarns and/or other conductive paths in item 10. Solder, conductive adhesive, or other conductive connections may be used in coupling pads 40 to conductive strands, printed circuit traces, or other conductive path materials in item 10.

Figure 7:
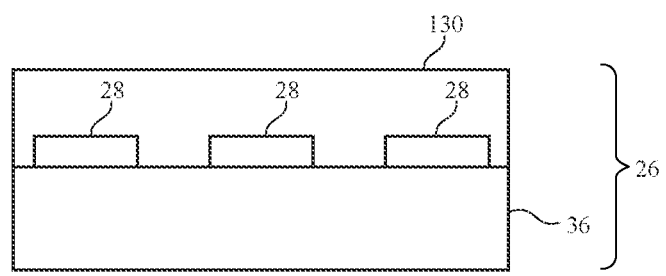
FIG. 7 is a cross-sectional side view of an illustrative electrical component having a protective structure in accordance with an embodiment.

FIG. 7 shows an example in which component 26 includes a protective structure such as protective structure 130 on interconnect substrate 36. Protective structure 130 may, for example, be a plastic structure that completely or partially encapsulates devices 28 and interconnect substrate 36 to provide mechanical robustness, protection from moisture and other environmental contaminants, heat sinking, and/or electrical insulation. Protective structure 130 may be formed from molded plastic (e.g., injection-molded plastic, insert molded plastic, transfer molded plastic, low-pressure molded plastic, two-part molded plastic, etc.) that has been molded over one or more devices 28 and substrate 36 or that is molded into the desired shape and subsequently attached to substrate 36, may be a layer of encapsulant material (e.g., thermoplastic) that has been melted to encapsulate devices 28, may be a layer of polymer such as polyimide that has been cut or machined into the desired shape and subsequently attached to substrate 36, or may be formed using other suitable methods. Illustrative materials that may be used to form protective structure 130 include epoxy, polyamide, polyurethane, silicone, thermoplastic, other suitable materials, or a combination of any two or more of these materials. Protective structure 130 may be formed on one or both sides of substrate 36 (e.g., may completely or partially surround substrate 36).

Protective structure 130 may be entirely opaque, may be entirely transparent, or may have both opaque and transparent regions. Transparent portions of protective structure 130 may allow light emitted from one or more devices 28 to be transmitted through protective structure 130 and/or may allow external light to reach (and be detected by) one or more devices 28. If desired, one or more openings, recesses, grooves, and/or other features may be formed in protective structure 130. For example, an opening may be formed in protective structure 130 to allow light to be detected by and/or emitted from one or more devices 28. Protective structure 130 may include one or more grooves for receiving strands (e.g., conductive or insulating strands) in fabric 12.

Protective structure 130 may, if desired, have different thicknesses. The example of FIG. 7 in which protective structure 130 has uniform thickness across substrate 36 is merely illustrative. In some arrangements, protective structure 130 may be an encapsulant material such as thermoplastic that has been melted to create a robust connection between component 26 and strands 80 of fabric 12. For example, protective structure 130 may surround portions of strands 80, may fill recesses, grooves, or other features in component 26 to help interlock component 26 to strands 80, and/or may fill gaps in fabric 12. Protective structure 130 may include one or more different types of materials, if desired (e.g., one or more different thermoplastic materials with different melting temperatures).

If desired, substrate 36 may be sufficiently large to accommodate multiple electrical devices each with a respective body 28. For example, one or more light-emitting diodes, sensors, microprocessors, and/or other electrical devices may be mounted to a common substrate such as substrate 36 of FIG. 7. The light-emitting diodes may be micro-light-emitting diodes (e.g., light-emitting diode semiconductor dies having footprints of about 10 microns×10 microns, more than 5 microns×5 microns, less than 100 microns×100 microns, or other suitable sizes). The light-emitting diodes may include light-emitting diodes of different colors (e.g., red, green, blue, white, etc.), infrared light, or ultraviolet light. Redundant light-emitting diodes or other redundant circuitry may be included on substrate 36. In configurations of the type shown in FIG. 7 in which multiple electrical devices (each with a respective body 28) are mounted on a common substrate, electrical component 26 may include any suitable combination of electrical devices (e.g., light-emitting diodes, sensors, integrated circuits, actuators, energy storage devices, and/or other devices of the type described in connection with electrical component 26 of FIG. 5).

The examples of FIGS. 6 and 7 in which devices 28 are only located on one side of substrate 36 are merely illustrative. If desired, devices 28 may be mounted to both sides of substrate 36.

Electrical components 26 may be coupled to fabric structures, individual strands, printed circuits (e.g., rigid printed circuits formed from fiberglass-filled epoxy or other rigid printed circuit board material or flexible printed circuits formed from polyimide substrate layers or other sheets of flexible polymer materials), metal or plastic parts with signal traces, or other structures in item 10.

Figure 8:
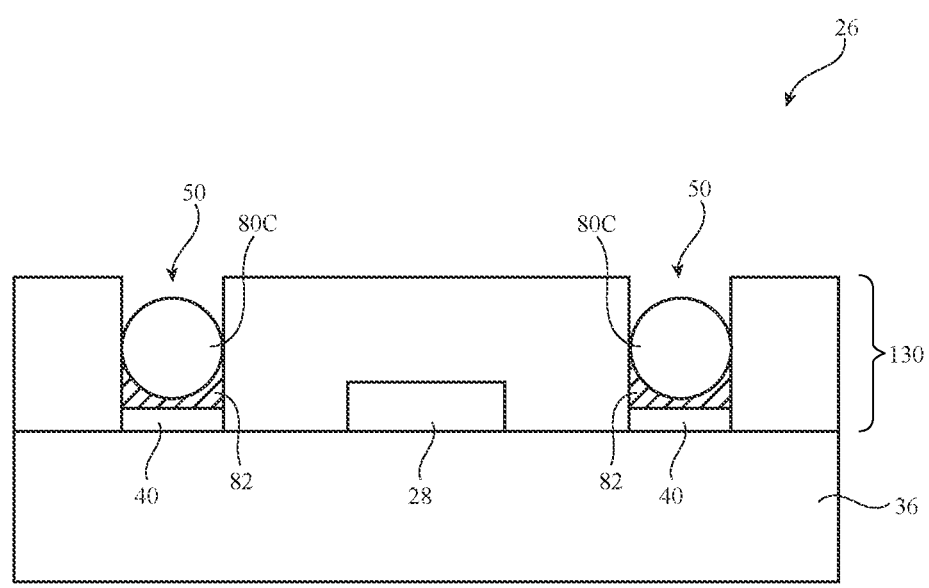
FIG. 8 is a cross-sectional side view of an illustrative electrical component having recesses for receiving strands in accordance with an embodiment.

In some configurations, item 10 may include electrical connections between components 26 and conductive paths in fabric 12. As shown in FIG. 8, for example, component 26 may be coupled to conductive strands 80C of fabric 12. Conductive strands 80C (sometimes referred to as "wires") may be configured to carry electrical signals (e.g., power, digital signals, analog signals, sensor signals, control signals, data signals, input signals, output signals, or other suitable electrical current) to and/or from components 26. Strands 80C may be warp strands (e.g., warp strands 20 of FIG. 2), weft strands (e.g., weft strands 22 of FIG. 2), or other suitable strands 80 in fabric 12. If desired, component 26 may be coupled to only a single conductive strand 80C, may be coupled to two conductive strands 80C, or may be coupled to three or more conductive strands 80C. If desired, component 26 may also or instead be coupled to insulating strands in fabric 12. Arrangements in which component 26 is coupled to a pair of conductive strands 80C are sometimes described herein as an illustrative example.

Component 26 may have contact pads such as pads 40. Conductive material 82 may be used to couple pads 40 to conductive strands 80C. Conductive material 82 may be solder, anisotropic conductive adhesive, or other conductive material. Arrangements in which conductive material 82 is formed from solder may sometimes be described herein as an illustrative example. In the example of FIG. 8, pads 40 are formed on the same surface of substrate 36 on which device 28 is mounted. Conductive material 82 may be used to electrically and mechanically couple component 26 to strands 80C of fabric 12. If desired, pads 40 may also or instead be additionally formed on the lower surface of substrate 36 (e.g., the surface opposite the surface on which device 28 is mounted). The example of FIG. 8 is merely illustrative.

In some configurations, it may be desirable to provide a more robust mechanical connection between component 26 and fabric 12 to ensure that component 26 does not come loose when fabric 12 is bent or stretched. To increase the robustness of the connection between strands 80C and component 26, component 26 may have one or more recesses for receiving strands 80C. For example, one or more strands 80 may be threaded through a portion of component 26 to help secure component 26 to fabric 12. Strands 80 may be threaded through openings (sometimes referred to as recesses, trenches, grooves, holes, slots, notches, etc.) of component 26. The openings may be formed in device 28, interconnect substrate 36, protective structure 130, and/or other portions of component 26. FIG. 8 shows an example in which conductive strands 80C are received within grooves such as grooves 50 that are formed in protective structure 130. This is, however, merely illustrative. If desired, grooves 50 may instead or additionally be formed in interconnect substrate 36, device 28, and/or other portions of component 26. The location, shape, and geometry of grooves 50 of FIG. 8 are merely illustrative.

Grooves 50 (sometimes referred to as recesses, trenches, openings, holes, slots, notches, etc.) in protective structure 130 may be formed by removing portions of protective structure 130 (e.g., using a laser, a mechanical saw, a mechanical mill, or other equipment) or may be formed by molding (e.g., injection molding, insert molding, etc.) or otherwise forming protective structure 130 into a shape that includes grooves 50. Grooves 50 may have a width between 2 mm and 6 mm, between 0.3 mm and 1.5 mm, between 1 mm and 5 mm, between 3 mm and 8 mm, greater than 3 mm, less than 3 mm, or other suitable width. If desired, grooves 50 may have different depths (e.g., to expose contact pads 40 that are located at different surface heights of interconnect substrate 36).

In the example of FIG. 8, grooves 50 expose conductive pads 40 on interconnect substrate 36. Strands 80C may each be threaded through an associated one of grooves 50 in protective structure 130. Solder or other conductive material 82 may be used to electrically and mechanically couple strands 80C to conductive pads 40 in grooves 50 of protective cover 130. Because strands 80C are wedged between portions of protective cover 130, strands 80C may be resistant to becoming dislodged from substrate 36. In addition to holding strands 80C in place so that component 26 remains attached to fabric 12, grooves 50 may also be used as a physical guide for aligning component 26 relative to fabric 12 during component insertion and attachment operations. This may be beneficial when inserting and attaching component 26 to fabric 12 without line of sight, for example.

Each strand 80C may align with an associated pad 40 on component 26. If desired, pads 40 may formed from elongated strips of conductive material (e.g., metal) that extend from one edge of substrate 36 to an opposing edge of substrate 36. This provides a large area with which to form a mechanical and electrical connection between substrate 36 and strands 80C. The elongated shape of pads 40 may allow conductive material 82 to attach a longer portion of strand 80C to pad 40. The connection between pad 40 and strand 80C may, for example, span across the width of substrate 36, thereby providing a robust connection between substrate 36 and strand 80C. This is, however, merely illustrative. If desired, pads 40, conductive material 82, and the exposed conductive portions of strands 80C may span across less than all of the width of component 26.

If desired, component 26 may include internal portions that are located within fabric 12 and external portions that are located on the outside of fabric 12. To allow mechanical and/or electrical connections between the internal and external portions of component 26, component 26 may include one or more protrusions that pass through fabric 12 to interconnect the internal and external portions of component 26. The internal portion of component 26 that is located within fabric 12 may be inserted into fabric 12 during the formation of fabric 12, as described in connection with FIG. 4. Following formation of fabric 12, the external portion of component 26 may be coupled to the internal portion via protrusions on component 26 that pass through fabric 12.

Figure 9:
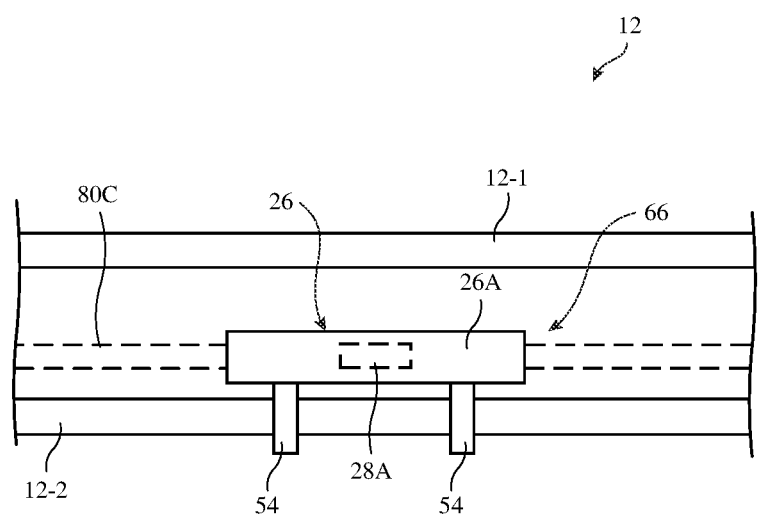
FIG. 9 is a cross-sectional side view of an illustrative electrical component having an internal portion located within a piece of fabric and having protrusions that protrude out of the fabric in accordance with an embodiment.

FIG. 9 is a cross-sectional side view of illustrative fabric 12 having a component with an internal portion located inside of the fabric and protrusions that allow the internal portion to be coupled to an external portion outside of the fabric. As shown in FIG. 9, fabric 12 may include upper and lower fabric portions 12-1 and 12-2. As discussed in connection with FIG. 4, fabric portions 12-1 and 12-2 may be formed from interlaced strands 80. For example, a first set of strands 80 may be used to form fabric portion 12-1 and a second set of strands 80 may be used to form fabric portion 12-2. Fabric portions 12-1 and 12-2 may be different portions of a single layer of fabric 12, or fabric portion 12-1 may form one or more first layers of fabric 12 and fabric portion 12-2 may form one or more second layers of fabric 12.

Interlacing equipment 120 of FIG. 4 may be used to create one or more regions in fabric 12 such as pocket 66 for receiving electrical components. In the example of FIG. 9, internal portion 26A of component 26 may be inserted into pocket 66 during the formation of fabric 12 (e.g., using component insertion equipment such as insertion tool 54 of FIG. 4). If desired, internal portion 26A may be electrically and/or mechanically connected to one or more strands in fabric 12 such as conductive strand 80C. Internal portion 26A may have grooves of the type shown in FIG. 8 for receiving strands such as strand 80C to provide a more robust electrical and mechanical connection between internal portion 26A and fabric 12. This is, however, merely illustrative. If desired, internal portion 26A may be coupled to an insulating strand 80 (e.g., without being electrically coupled to fabric 12) or may not be connected to any strands 80 (e.g., internal portion 26A may be contained within pocket 66 without being mounted to any strands).

Internal portion 26A of component 26 may include one or more electrical devices 28A. Electrical device 28A may include any of the circuitry described in connection with FIG. 5. In one illustrative arrangement, device 28A of internal portion 26A includes control circuitry for controlling one or more electrical devices in an external portion of component 26 (not shown in FIG. 9). This is merely illustrative, however. If desired, the circuitry in internal portion 26A of component 26 may operate independently of any circuitry in an external portion of component 26.

To provide an electrical and/or mechanical connection between the internal and external portions of component 26, component 26 may include protruding portions such as protruding portions 54 that pass through fabric 12-2. Protruding portions 54 may be leads, pins, posts, flexible wires, and/or any other suitable structures extending from within fabric 12 (e.g., in pocket 66) to the exterior of fabric 12 (e.g., to be exposed on an outer surface of fabric 12). Protrusions 54 may be formed from conductive material to allow electrical signals to pass between the internal and external portions of component 26, or protrusions 54 may be used exclusively for mechanical connection between the internal and external portions of component 26.

Protrusions 54 may, for example, be formed as part of internal portion 26A of component 26. When internal portion 26A is inserted into fabric 12 during the formation of fabric 12, protrusions 54 may initially be located within fabric 12 (e.g., between fabric portions 12-1 and 12-2. When internal portion 26A is received within pocket 66, protrusions 54 may naturally extend through fabric 12 (e.g., through fabric portion 12-2, in the example of FIG. 9), or protrusions 54 may extend through fabric 12 after internal portion 26A is pressed toward fabric 12 (e.g., during formation of fabric 12 or after formation of fabric 12). Protrusions 54 may extend between adjacent strands 80 (e.g., between gaps that already exist between strands 80), may extend through individual strands 80, and/or may extend through openings that are specifically formed in fabric 12 for receiving protrusions 54. There may be one, two, three, four, or more than four protrusions extending from internal portion 26A through fabric 12.

After formation of fabric 12, internal portion 26A may be contained within fabric 12 and protrusions 54 may be exposed on the exterior of fabric 12. This allows an external portion of component 26 to be coupled to the internal portion of component 26 after fabric 12 is formed, as shown in FIG. 10.

Figure 10:
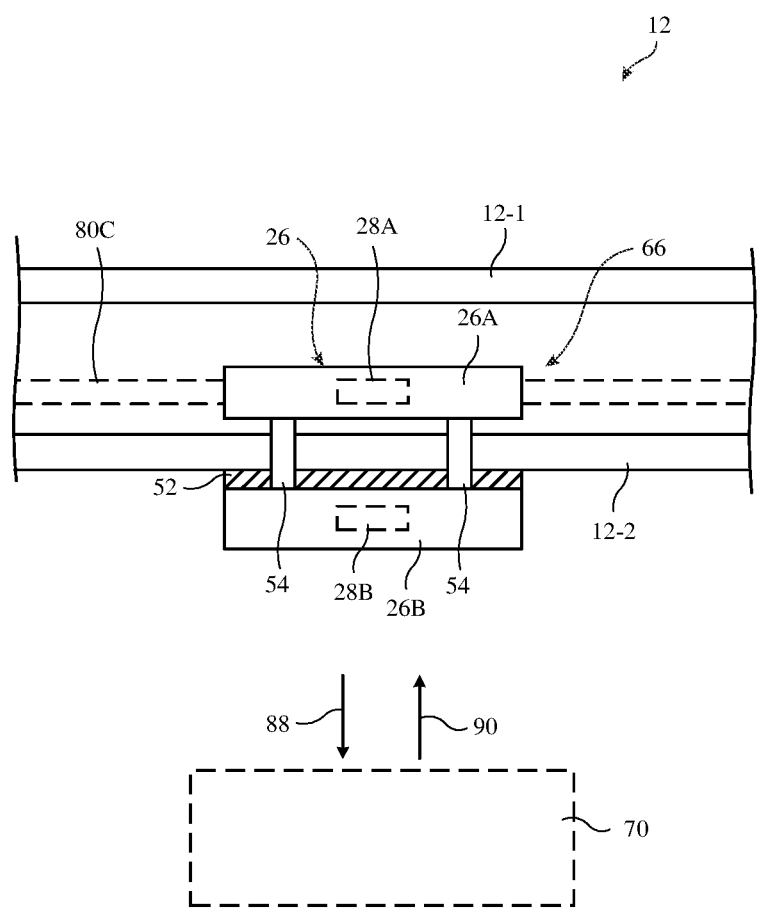
FIG. 10 is a cross-sectional side view of an illustrative electrical component of the type shown in FIG. 9 with an external portion located outside of the fabric in accordance with an embodiment.

As shown in FIG. 10, external portion 26B of component 26 may overlap and be coupled to internal portion 26A by attaching external portion 26B to protrusions 54. External portion 26B of component 26 may include electrical devices 28B. Devices 28B may include any of the circuitry described in connection with FIG. 5. For example, devices 28B may include circuitry that is controlled by or otherwise in electrical communication with devices 28A of internal portion 26A.

By forming part of component 26 inside of fabric 12 and another part of component 26 outside of fabric 12, input-output components that operate better outside of fabric (e.g., optical components such as optical sensors, cameras, displays, indicators, speakers, microphones, removable and/or replaceable batteries, haptic output devices, etc.) may be formed on an exterior surface of fabric 12, while internal circuitry (e.g., control circuitry, logic boards, printed circuits, driver circuitry, etc.) may be hidden or otherwise contained within an interior portion of fabric 12. This allows signals to be emitted from external portion 26B of component 26 and/or detected by external portion 26B of component 26 without interference from fabric 12. For example, external portion 26B of component 26 may emit signals in direction 88 towards object 70 and/or may detect signals coming from object 70 in direction 90 without interference from fabric 12. Signals that are emitted and/or detected by external portion 26B of component 26 may include optical signals, radio-frequency signals, haptic signals, ultrasonic signals, sound signals, capacitive signals, and/or any other suitable signals.

In one illustrative arrangement, fabric 12 may form a fabric band that is worn around a user's wrist or other body part. External portion 26B may be an optical component such as a heart-rate sensor (e.g., a photoplethysmography sensor), a blood oxygen sensor, or other optical sensor that rests against a user's skin (or a non-optical heart-rate sensor such as electrocardiographic electrodes that rest against the skin). Internal portion 26A may include control circuitry for controlling the optical component(s) in external portion 26B and/or for monitoring output from the optical component(s) in external portion 26B and taking suitable action (e.g., providing output associated with sensor data gathered by the optical component(s) in external portion 26B). By mounting control circuitry in internal portion 26A within fabric 12 and skin-facing sensors in external portion 26B outside of fabric 12, sensors may be better positioned for accurate heart rate measurements while a bulk of the circuitry associated with the sensors may be hidden from view within fabric 12. This is merely illustrative, however. In general, any suitable circuitry may be located within internal and external portions of component 26.

The arrangement of FIG. 10 in which internal portion 26A and external portion 26B have a similar lateral footprint is merely illustrative. If desired, internal portion 26A may have a smaller or larger lateral footprint than external portion 26B.

External portion 26B of component 26 may include mating attachment structures (e.g., recesses, mating pins, solder pads, screw holes, etc.) configured to mate with protrusions 54 to provide an electrical and/or mechanical connection between internal portion 26A and external portion 26B. This is merely illustrative. If desired, protrusions 54 may be formed on external portion 26B of component 26, and internal portion 26A of component 26 may include mating attachment features that mate with protrusions 54. In this type of configuration, protrusions on external portion 26B of component 26 may be attached to internal portion 26A of component 26 by inserting the protrusions on external portion 26B through fabric 12 after fabric 12 is formed to connect to internal portion 26A.

If desired, an adhesive layer such as adhesive layer 52 may be used to attach external portion 26B to the exterior surface of fabric 12 (e.g., fabric portion 12-2 in the example of FIG. 10). Adhesive layer 52 may serve as a watertight seal that prevents moisture and/or other contaminants from entering into the connection region between internal and external portions of component 26. In arrangements where external portion 26B is removable (e.g., when external portion 26B is a removable battery or other removable component), adhesive 52 may be omitted.

In addition to or instead of adhesive between external portion 26B and fabric 12, an encapsulating border may be formed around external portion 26B to seal the connection between external portion 26B and fabric 12. This type of arrangement is illustrated in FIG. 11.

Figure 11:
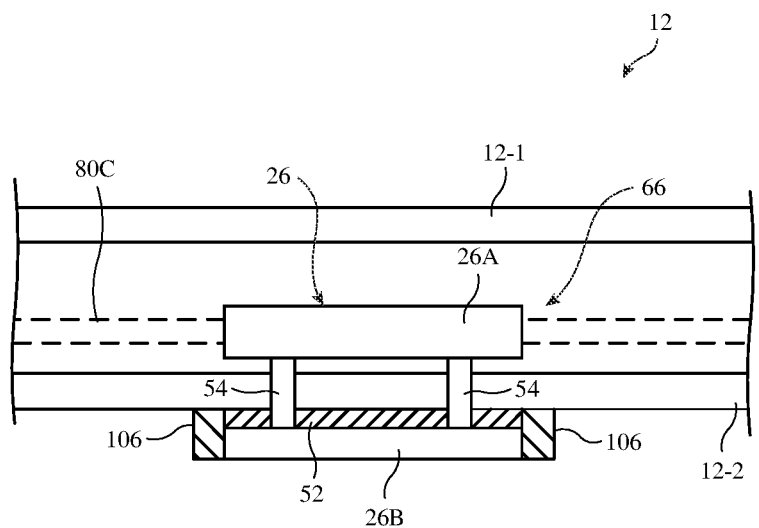
FIG. 11 is a cross-sectional side view of an illustrative electrical component having a protective encapsulant around an external portion in accordance with an embodiment.

As shown in FIG. 11, encapsulating border 106 may be located along an outer perimeter of external portion 26B and may form a protective ring around external portion 26B. Encapsulating border 106 may be formed from thermosetting material, thermoplastic material, adhesive, epoxy, and/or any other suitable material for preventing moisture and/or other contaminants from reaching the electrical and/or mechanical connection between external portion 26B of component 26 and the internal portion 26A of component 26.

Figure 12:
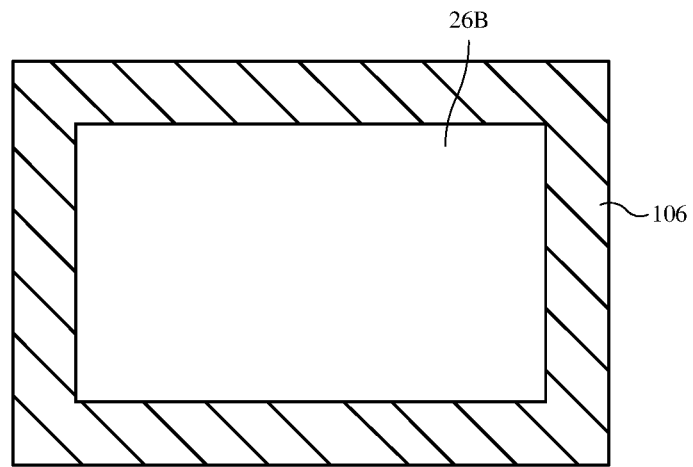
FIG. 12 is a top view of a protective encapsulant of the type shown in FIG. 11 surrounding an external portion of an electrical component in accordance with an embodiment.

As shown in the top view of FIG. 12, encapsulating border 106 may form a rectangular ring around external portion 26B of component 26. This is merely illustrative, however. If desired, encapsulating border 106 may have non-rectangular shapes and/or may only partially surround external portion 26B of component 26.

Figure 13:
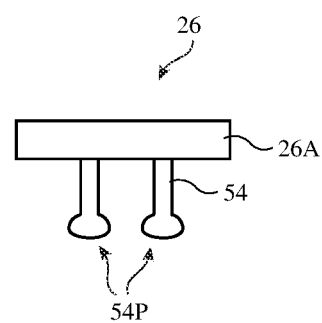
FIG. 13 is a cross-sectional side view of an illustrative electrical component having protrusions with spherical ends in accordance with an embodiment.
Figure 14:
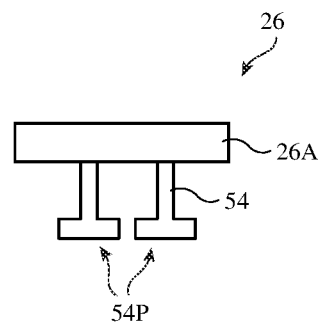
FIG. 14 is a cross-sectional side view of an illustrative electrical component having protrusions with T-shaped ends in accordance with an embodiment.
Figure 15:
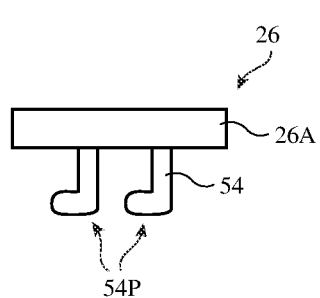
FIG. 15 is a cross-sectional side view of an illustrative electrical component having protrusions with L-shaped ends in accordance with an embodiment.

FIGS. 13, 14, and 15 are side views showing illustrative shapes of protrusions 54. Protrusions 54 are illustrated as being part of internal portion 26A, but may be part of external portion 26B, if desired.

In the example of FIG. 13, protrusions 54 have end portions 54P with spherical shapes (e.g., balls). External portion 26B of component 26 may have mating recesses with shapes that are specifically designed to receive ball-shaped protrusions 54P of FIG. 13.

In the example of FIG. 14, protrusions 54 have end portions 54P with T shapes. External portion 26B of component 26 may have mating recesses with shapes that are specifically designed to receive T-shaped protrusions 54P of FIG. 14.

In the example of FIG. 15, protrusions 54 have end portions 54P with L shapes. External portion 26B of component 26 may have mating recesses with shapes that are specifically designed to receive L-shaped protrusions 54P of FIG. 15. The examples of FIGS. 13, 14, and 15 are merely illustrative. Other shapes may be used, if desired.

Figure 16:
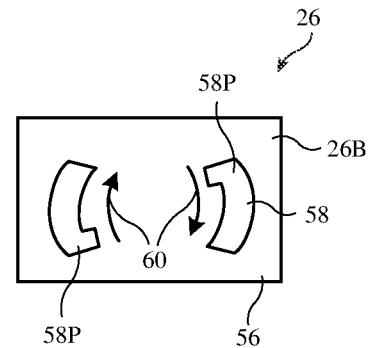
FIG. 16 is a top view of an illustrative external portion of an electrical component having recesses for receiving protrusions on an internal portion of the electrical component in accordance with an embodiment.

FIG. 16 shows how external portion 26B of component 26 may have a surface 56 with recesses such as curved recesses 58 for receiving protrusions 54 of internal portion 26A of component 26. Providing recesses 58 with a curved shape allows for a robust mechanical connection in which end portions 54P of protrusions 54 are first inserted into wider end regions 58P of recesses 58 and subsequently rotated in directions 60, thereby locking external portion 26B into place on internal portion 26A. Wider end regions 58P may be shaped to receive the wider end portions 54P of protrusions 54, while the rest of recess 58 may be sufficiently narrow such that wider end portions 54P are unable to pass through. When it is desired to remove external portion 26B from internal portion 26A, external portion 26B may be rotated in the opposite direction so that each end portion 54P can slide within recess 58 to exit recess 58 at end regions 58P.

Figure 17:
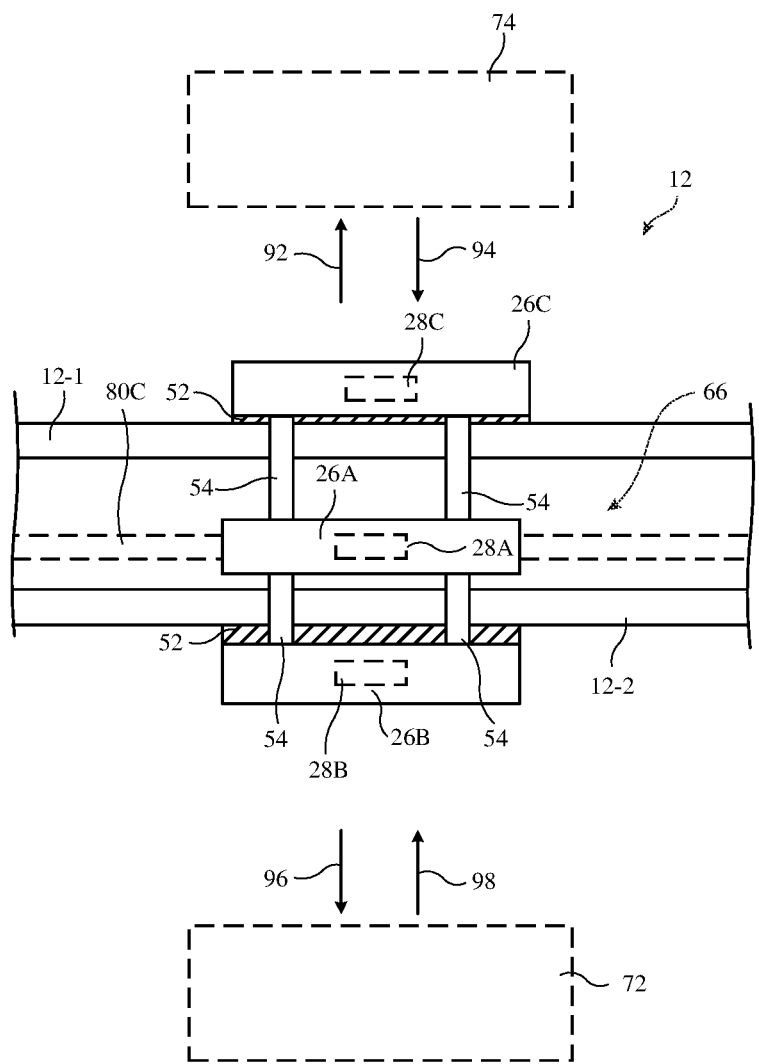
FIG. 17 is a cross-sectional side view of an illustrative electrical component having an internal portion located within a piece of fabric and coupled to first and second external portions located outside of the fabric in accordance with an embodiment.

FIG. 17 is a cross-sectional side view showing an illustrative example in which internal portion 26A of component 26 is coupled to upper and lower external portions 26B and 26C.

As shown in FIG. 17, a first external portion such as external portion 26B of component 26 may be coupled to internal portion 26A by attaching external portion 26B to a first set of protrusions 54 on a first side of internal portion 26A (e.g., a side facing fabric portion 12-2). A second external portion such as external portion 26C of component 26 may be coupled to internal portion 26A by attaching external portion 26B to another set of protrusions 54 on a second opposing side of internal portion 26A (e.g., a side facing fabric portion 12-1). If desired, adhesive 52 may be used to attach external portion 26C to an exterior surface of fabric portion 12-1.

External portion 26B of component 26 may include one or more electrical devices 28B, and external portion 26C of component 26 may include one or more electrical devices 28C. Devices 28B and 28C may include any of the circuitry described in connection with FIG. 5. For example, devices 28B and 28C may include circuitry that is controlled by or otherwise in electrical communication with devices 28A of internal portion 26A.

The arrangement of FIG. 17 allows signals to be emitted from external portions 26B and 26C of component 26 and/or detected by external portions 26B and 26C of component 26 without interference from fabric 12. For example, external portion 26B of component 26 may emit signals in direction 96 towards object 72 and/or may detect signals coming from object 72 in direction 98 without interference from fabric 12. External portion 26C of component 26 may emit signals in direction 92 towards object 74 and/or may detect signals coming from object 74 in direction 94 without interference from fabric 12.

Signals that are emitted and/or detected by external portion 26B and/or external portion 28C of component 26 may include optical signals, radio-frequency signals, haptic signals, ultrasonic signals, sound signals, capacitive signals, and/or any other suitable signals.

In one illustrative arrangement, fabric 12 may form a fabric band that is worn around a user's wrist or other body part. External portion 26B may be a skin-facing input-output device (e.g., an optical component such as a heart-rate sensor, a blood oxygen sensor, or other optical sensor that rests against a user's skin, a non-optical heart-rate sensor such as electrocardiographic electrodes, a haptic output device that provides haptic output to a user, etc.), while external portion 26C may be a viewer-facing input-output device such as a display, an indicator, a camera, a button, a rotating knob, a touch screen or other touch sensor, a fingerprint sensor, and/or any other suitable input-output component that the user may want to look at during use.

Internal portion 26A may include control circuitry for controlling the input-output component(s) in external portions 26B and 26C and/or for monitoring output from the input-output component(s) in external portions 26B and 26C and taking suitable action. By mounting control circuitry in internal portion 26A within fabric 12 and skin-facing or viewer-facing input-output components in external portions 26B and 26C outside of fabric 12, input-output components may be better positioned for the desired input-output capabilities without interference from fabric 12, while a bulk of the circuitry associated with the input-output components may be hidden from view within fabric 12. This is merely illustrative, however. In general, any suitable circuitry may be located within internal and external portions of component 26.

Figure 18:
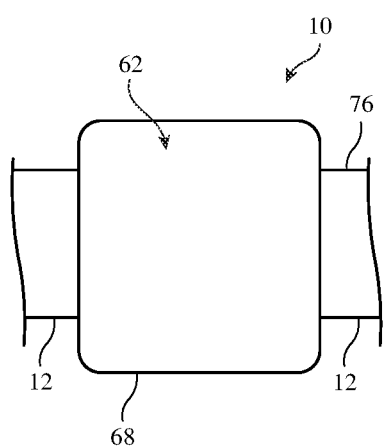
FIG. 18 is a top view of an illustrative electronic device such as a watch having a fabric strap that incorporates one or more electrical components in accordance with an embodiment.

In some arrangements, fabric 12 with electrical components having internal and external portions may be used to form a strap for a wearable device such as a watch. This type of arrangement is illustrated in FIG. 18. Device 10 may be worn on a body part of a user (e.g., the user's wrist, arm, head, leg, or other portion of the user's body). As an example, device 10 may include a wearable band, such as band 76 of FIG. 18. Band 76, which may sometimes be referred to as a wristband, wrist strap, or wristwatch band, may be formed from polymer, metal, fabric, leather or other natural materials, and/or other material, may have links, may stretch, may be attached to housing 68 in a fixed arrangement, may be detachably coupled to housing 68, may have a single segment or multiple segments joined by a clasp, and/or may have other features that facilitate the wearing of device 10 on a user's wrist. Housing 68 may be formed from polymer, metal, glass, crystalline material such as sapphire, ceramic, fabric, fibers, fiber composite material, natural materials such as wood and cotton, other materials, and/or combinations of such materials.

Device 10 may include one or more displays such as display 62. The displays may, for example, include an organic light-emitting diode display, a liquid crystal display, a display having an array of pixels formed from respective light-emitting diodes (e.g., a pixel array having pixels with light-emitting diodes formed from respective crystalline light-emitting diode dies such as micro-light-emitting diode dies), and/or other displays. The displays may include rigid display structures and/or may be flexible displays. For example, a light-emitting diode display may have a polymer substrate that is sufficiently flexible to be bent. Display 62 may have a rectangular pixel array or a pixel array of another shape for displaying images for a user and may therefore sometimes be referred to as a pixel array. Display 62 may also sometimes be referred to as a display panel, display layer, or pixel layer. Each pixel array in device 10 may be mounted under a transparent housing structure (sometimes referred to as a transparent display cover layer, protective cover layer structures, etc.).

Figure 19:
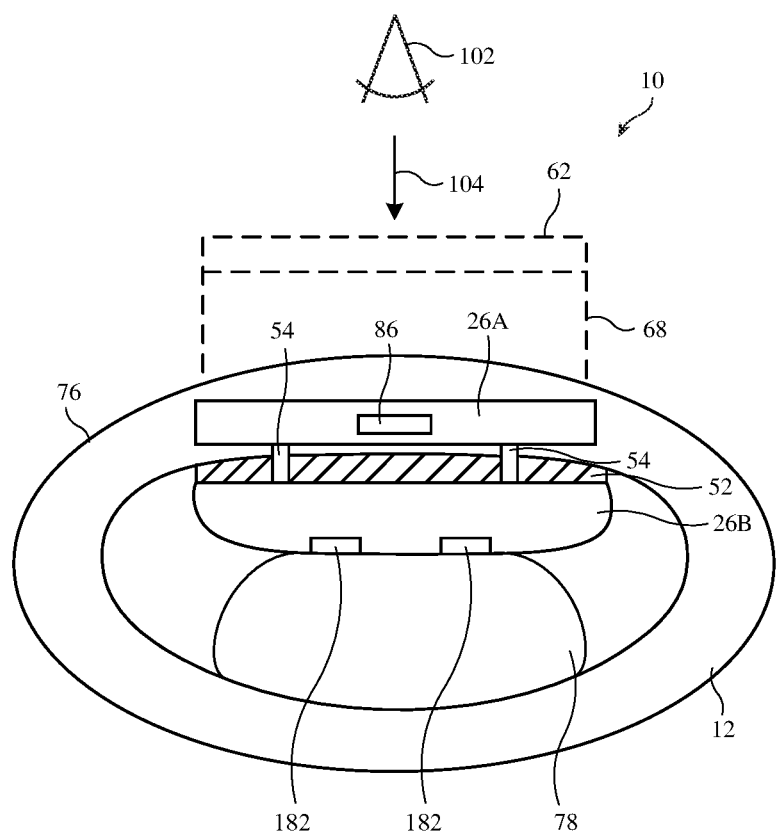
FIG. 19 is a cross-sectional side view of an illustrative electronic device of the type shown in FIG. 18 with a fabric strap that incorporates an electrical component having an internal portion located within the fabric and an external portion located outside of the fabric in accordance with an embodiment.

FIG. 19 is a cross-sectional side view of device 10 of FIG. 18. In the example of FIG. 19, device 10 is worn around a user's body part such as wrist 78. Strap 76 may extend partially or entirely around wrist 78 and may include one or more clasps, buckles, or other attachment mechanisms for removable coupling device 10 to wrist 78. Strap 76 may be formed from fabric 12 and may include one or more electrical components such as component 26. Component 26 may include an internal portion such as internal portion 26A located within fabric 12 and one or more external portions such as external portion 26B located on an exterior surface of fabric 12 (e.g., as described in connection with FIGS. 9-17). Internal portion 26A may be inserted into fabric 12 during the formation of fabric 12 and may have protrusions 54 that protrude through fabric 12. External portion 26B may be coupled to internal portion 26A after fabric 12 is formed. External portion 26B may have mating attachment structures such as mating recesses and/or mating protrusions that mate with protrusions 54 to mechanically and/or electrically couple external portion 26B to internal portion 26A.

Adhesive 52 (and/or an encapsulating border such as encapsulating border 106 of FIGS. 11 and 12) may be used to create a seal between external portion 26B and fabric 12.

In the example of FIG. 19, external portion 26B may form a back crystal module of device 10 with one or more skin-facing optical sensors. For example, external portion 26B may include one or more light-emitting devices 182 (e.g., one or more light-emitting diodes or lasers operating at visible and/or infrared wavelengths) and/or one or more light detectors 84 (e.g., a photodiode and/or other suitable light sensor). Light-emitting device 182 may emit light towards wrist 78 and light detector 84 may detect light that is reflected back from wrist 78. Internal portion 26A of component 26 may include control circuitry such as control circuitry 86. Control circuitry 86 may send control signals to light-emitting diode 182 and/or light detector 84 and/or may receive sensor data from light-detector 84 via protrusions 54.

If desired, housing 68 and display 62 may be formed on an opposing surface of fabric 12, so that viewer 102 can view display 62 in direction 104. Housing 68 and display 62 may, if desired, be electrically connected to internal portion 26A (e.g., via conductive strands 80C in fabric 12, via conductive protrusions 54 on an upper side of internal portion 26A as in the example of FIG. 17, and/or via other conductive structures in device 10). This is, however, merely illustrative. If desired, housing 68 and display 62 may not be electrically connected to component 26 (e.g., data may be wirelessly transferred between circuitry in housing 68 and circuitry in component 26).

As described above, one aspect of the present technology is the gathering and use of information such as information from input-output devices. The present disclosure contemplates that in some instances, data may be gathered that includes personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, username, password, biometric information, or any other identifying or personal information.

The present disclosure recognizes that the use of such personal information, in the present technology, can be used to the benefit of users. For example, the personal information data can be used to deliver targeted content that is of greater interest to the user. Accordingly, use of such personal information data enables users to have control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the United States, collection of or access to certain health data may be governed by federal and/or state laws, such as the Health Insurance Portability and Accountability Act (HIPAA), whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, the present technology can be configured to allow users to select to "opt in" or "opt out" of participation in the collection of personal information data during registration for services or anytime thereafter. In another example, users can select not to provide certain types of user data. In yet another example, users can select to limit the length of time user-specific data is maintained. In addition to providing "opt in" and "opt out" options, the present disclosure contemplates providing notifications relating to the access or use of personal information. For instance, a user may be notified upon downloading an application ("app") that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of information that may include personal information data to implement one or more various disclosed embodiments, the present disclosure also contemplates that the various embodiments can also be implemented without the need for accessing personal information data. That is, the various embodiments of the present technology are not rendered inoperable due to the lack of all or a portion of such personal information data.

The foregoing is merely illustrative and various modifications can be made by those skilled in the art without departing from the scope and spirit of the described embodiments. The foregoing embodiments may be implemented individually or in any combination.

What is claimed is:

1. A fabric item, comprising:
   first and second fabric portions that overlap one another and that form a closed pocket;
   an electrical component, comprising:
     an internal portion located in the closed pocket between the first and second fabric portions;
     an external portion located on an exterior surface of the second fabric portion, wherein the external portion overlaps the internal portion and wherein the second fabric portion is interposed between the internal portion and the external portion; and
     protrusions that extend through the second fabric portion and that couple the internal portion to the external portion; and
   adhesive interposed between the external portion and the second fabric portion.

2. The fabric item defined in claim 1 wherein the protrusions comprise a conductive material that conveys electrical signals between the internal portion and the external portion.

3. The fabric item defined in claim 1 wherein the external portion comprises an input-output device and the internal portion comprises control circuitry that is electrically coupled to the input-output device via the protrusions.

4. The fabric item defined in claim 3 wherein the input-output device comprises an optical sensor having a light-emitting diode and a light detector.

5. The fabric item defined in claim 4 wherein the optical sensor is selected from the group consisting of: a heart-rate sensor and a blood oxygen sensor.

6. The fabric item defined in claim 1 further comprising a conductive strand that passes between the first and second fabric portions, wherein the internal portion of the electrical component is mounted to the conductive strand.

7. The fabric item defined in claim 1 wherein the protrusions extend from the internal portion and wherein the external portion comprises recesses that receive the protrusions.

8. The fabric item defined in claim 7 wherein the recesses have a curved shape and wherein the protrusions are configured to slide within the recesses as the external portion is rotated relative to the internal portion.

9. The fabric item defined in claim 1 wherein the first and second fabric portions form a wrist strap.

10. The fabric item defined in claim 1 further comprising an encapsulating border located on the exterior surface of the second fabric portion that surrounds a periphery of the external portion.

11. A strap, comprising:
    fabric formed from interlaced strands of material, wherein the fabric has first and second fabric portions that overlap one another and that form a closed pocket; and
    an electrical component having a first portion located inside the closed pocket of the fabric, a second portion located outside of the fabric overlapping the first portion, and pins that extend through the fabric to couple the first portion to the second portion, wherein the second portion comprises a skin-facing optical sensor and the first portion comprises control circuitry that electrically communicates with the skin-facing optical sensor via the pins.

12. The strap defined in claim 11 wherein the skin-facing optical component comprises a light-emitting diode and a light detector.

13. The strap defined in claim 12 wherein the skin-facing optical component is selected from the group consisting of: a heart-rate sensor and a blood oxygen sensor.

14. The strap defined in claim 11 further comprising an adhesive interposed between the second portion and the fabric.

15. The strap defined in claim 11 wherein the strands of material comprise a conductive strand and wherein the first portion is mounted to the conductive strand inside of the fabric.

16. An electronic device, comprising:
    fabric formed from interlaced strands, wherein the fabric has first and second fabric portions that overlap one another and that form a closed pocket; and
    an electrical component comprising:
      an internal portion located in the closed pocket;
      an external portion uncovered by the fabric and exposed on an exterior surface of the fabric overlapping the internal portion; and
      pins that pass through the fabric to electrically couple the internal portion to the external portion.

17. The electronic device defined in claim 16 wherein the external portion has recesses that receive the pins.

18. The electronic device defined in claim 17 wherein the external portion is removably coupled to the internal portion by rotating the external portion relative to the internal portion.

19. The electronic device defined in claim 18 wherein the external portion comprises a removable battery.

* * * * *